US011096758B2

(12) United States Patent
Morey et al.

(10) Patent No.: US 11,096,758 B2
(45) Date of Patent: Aug. 24, 2021

(54) SURGICAL GUIDANCE SYSTEMS, DEVICES, AND METHODS

(71) Applicant: Boston Scientific Limited, St. Michael (BB)

(72) Inventors: Subodh Morey, Goa (IN); Ashish Jain, Uttar Pradesh (IN); Timothy Harrah, Cambridge, MA (US); Biten Kathrani, Maharashtra (IN); Sumit Malik, Haryana (IN); Salman Kapadia, Madhya Pradesh (IN); Charudatta Aradhye, Maharashtra (IN); Nishant Randhawa, Punjab (IN); Rajiv Kumar Singh, Thane (IN); Prashant Borkar, Maharashtra (IN)

(73) Assignee: Boston Scientific Limited, St. Michael (BB)

( * ) Notice: Subject to any disclaimer, the term of this patent is extended or adjusted under 35 U.S.C. 154(b) by 369 days.

(21) Appl. No.: 15/986,435

(22) Filed: May 22, 2018

(65) Prior Publication Data

US 2018/0338812 A1 Nov. 29, 2018

Related U.S. Application Data

(60) Provisional application No. 62/509,899, filed on May 23, 2017.

(51) Int. Cl.
*A61B 90/11* (2016.01)
*A61B 17/34* (2006.01)
(52) U.S. Cl.
CPC .......... *A61B 90/11* (2016.02); *A61B 17/3403* (2013.01)

(58) Field of Classification Search
CPC ..... A61B 90/10; A61B 90/11; A61B 17/3403; A61B 2017/3405; A61B 2017/3407
See application file for complete search history.

(56) References Cited

U.S. PATENT DOCUMENTS

| | | | |
|---|---|---|---|
| 4,899,756 A | 2/1990 | Sonek | |
| 5,758,650 A | 6/1998 | Miller et al. | |
| 6,689,142 B1* | 2/2004 | Tremaglio, Jr. ... | A61B 17/3403 604/114 |
| 2004/0122446 A1 | 6/2004 | Solar | |
| 2004/0260312 A1* | 12/2004 | Magnusson ........ | A61B 17/3403 606/130 |
| 2007/0106305 A1* | 5/2007 | Kao ....................... | A61B 90/11 606/130 |
| 2010/0042111 A1* | 2/2010 | Qureshi ................ | F16M 11/36 606/130 |
| 2010/0082040 A1 | 4/2010 | Sahni | |

(Continued)

FOREIGN PATENT DOCUMENTS

| | | |
|---|---|---|
| EP | 0207452 A2 | 1/1987 |
| WO | WO2012/051292 A1 | 4/2012 |

*Primary Examiner* — Melanie R Tyson
(74) *Attorney, Agent, or Firm* — Bookoff McAndrews, PLLC

(57) ABSTRACT

A guidance device may include a base member, a support coupled to the base member via at least one leg, thereby defining a passage configured to receive an accessory device between the base member and the support, and a guide coupled to the support. The guide may be movable relative to the base member and may include a through hole extending therethrough.

12 Claims, 9 Drawing Sheets

(56) References Cited

U.S. PATENT DOCUMENTS

| | | | |
|---|---|---|---|
| 2012/0022368 A1* | 1/2012 | Brabrand | A61B 90/11 600/427 |
| 2013/0158578 A1* | 6/2013 | Ghodke | A61B 17/320783 606/170 |
| 2014/0163356 A2 | 6/2014 | Burnside et al. | |
| 2014/0336670 A1 | 11/2014 | Brabrand et al. | |
| 2015/0190151 A1* | 7/2015 | Budhabhatti | A61B 17/17 606/96 |
| 2016/0367331 A1* | 12/2016 | Nelson | A61B 90/10 |
| 2016/0367332 A1* | 12/2016 | Shah | A61B 90/11 |
| 2017/0086813 A1 | 3/2017 | Hess et al. | |

* cited by examiner

SURGICAL GUIDANCE SYSTEMS, DEVICES, AND METHODS

CROSS-REFERENCE TO RELATED APPLICATIONS

This patent application claims the benefit of priority under 35 U.S.C. § 119 to U.S. Provisional Patent Application No. 62/509,899, filed May 23, 2017, which is herein incorporated by reference in its entirety.

TECHNICAL FIELD

Aspects of the present disclosure generally relate to medical devices and procedures. In particular, some aspects relate to surgical guidance systems, devices, and methods.

BACKGROUND

Non-invasive surgical procedures enable a medical professional to treat an internal area of a body while minimizing a size of a physical opening in the exterior skin of the body. Many non-invasive procedures are designed to treat a particular area of the body, such as an organ. Percutaneous nephrolithonomy (or "PCNL"), for example, is one such procedure, wherein an object, such as a needle, is inserted through the skin and into a kidney for removal of a kidney stone. Precise placement of the needle is required to avoid damaging the kidney or surrounding tissues. Therefore, medical imaging techniques, such as fluoroscopy, may be used in PCNL procedures to both locate a kidney and track the location of the needle with respect to the located kidney. Even with the aid of fluoroscopy, however, a medical professional must have a detailed understanding of the anatomy in and around the kidney so as to be able to visualize the kidney and surrounding tissues when making a puncture through the skin. As such, the step of gaining access to the kidney via a puncture through the skin may necessitate a medical professional having significant experience and/or the assistance of a radiologist to ensure the accurate location and angle of access to the kidney through a puncture in the skin. Additionally, once access has been gained, a medical professional must ensure that the needle is not inadvertently moved so as to avoid injury to surrounding tissue.

The systems, devices, and methods of the current disclosure may rectify or lessen some of the challenges described above, and/or address other aspects of the prior art.

SUMMARY

Aspects of the present disclosure relate to, among other things, systems, devices, and methods for surgical guidance. Each of the aspects disclosed herein may include one or more of the features described in connection with any of the other disclosed aspects.

In one example, a guidance device may include a base member, a support coupled to the base member, and a guide coupled to the support. The guide may be movable relative to the base member and may include a through hole extending therethrough.

Examples of the guidance device may include one or more of the following features. The support may include a ball socket and the guide may include a ball. The ball may be movably received within the support. The guide may include a radiopaque member extending about a circumference of the ball. The device may further include a lock, and in a locked configuration, the lock frictionally engages the ball. The support may include at least one arm having a rail and the guide may include a support bed movably coupled to the rail. The at least one arm may be rotatable about a central axis of the base member and relative to the base member. The support bed may be movable about an axis perpendicular to the central axis of the base member along the rail. The support bed may include a radiopaque member extending about at least a portion of the support bed. The support may further include a support member received within and rotatable about a channel of base member. The device may further include a plurality of tabs coupled to the base member. At least some of the plurality of tabs may be deflectable toward a plane of the base member via a living hinge. At least some of the plurality of tabs may include an adhesive thereon. A proximal opening of the through hole of the guide may be tapered. The base may include a c-shaped ring or plate.

In a further example, a method may include positioning a base member of a guidance device at a location on skin of a patient. The method may further include adjusting an angular orientation of a guide movably coupled to the base member. The guide may include a ball housed within a mount. Additionally, the method may include securing the base member to the skin of the patient, and deploying an insertion device through the ball and into the patient.

Examples of the method may include one or more of the following features. The method may include confirming an orientation of the insertion device via a radiopaque member positioned on the ball. The securing the base member to the skin may include deflecting at least one tab coupled to the base member towards the skin of the patient. The method may further include frictionally engaging the ball via a lock so as to prevent movement of the ball relative to the mount.

In a further example, a guidance device may include a base member having a central axis, a mount coupled to the base member, and a ball rotatably received within the mount. The ball may include a radiopaque member about a circumference of the ball. The ball may be rotatable about a ball axis which is coaxial with or angled with respect to central axis.

Examples of the guidance device may include one or more of the following features. The device may further include a lock, and in a locked configuration, the lock may frictionally engage the ball. A plurality of tabs may be coupled to the base member. At least some of the plurality of tabs may be deflectable toward a plane of the base member via a living hinge. At least some of the plurality of tabs may include an adhesive thereon.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate exem

DETAILED DESCRIPTION

Examples of the present disclosure relate to surgical guidance systems, devices, and methods for treating internal areas of a subject's body. Such a surgical guidance system may include a base and at least one insertion device associated with the base for insertion into an organ (e.g., a kidney) of a patient via a puncture in the skin of the patient. Additionally, such a surgical guidance system may facilitate tracking the location of an object relative to the body of the patient.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative and directional positions of the components of an exemplary base or insertion device. When used herein, "proximal" refers to a position closer to the exterior of the body of the patient or closer to an operator and/or medical professional using the base or insertion device. In contrast, "distal" refers to a position further away from the operator and/or medical professional using the base or insertion device, or closer to the interior of the body of the patient.

While aspects of the present disclosure are described in reference to a surgical guidance system in conjunction with medical imaging technology to track a position of an insertion device (e.g., needle) relative to a kidney of a patient, the disclosure is not so limited. Rather, any reference to a particular type of medical procedure (e.g., PCNL), insertion device (e.g., needle), area of the treatment (e.g., kidney), or medical imaging technology (e.g., fluoroscopy) is provided for convenience and not intended to limit the present disclosure. Accordingly, the exemplary surgical guidance systems, devices, and methods described herein may be utilized for or with any other appropriate procedure, insertion device, area of treatment, or imaging technology, medical or otherwise. For example, other energy emitting devices similar to fluoroscopes may be suitable for use with devices and methods according to the present disclosure. Additionally, although some of the arrangements described herein refer to only radiopaque materials for use as an imaging reference material, other types of imaging reference materials may be used in connection with other imaging systems (such as ultrasound, MRI or CAT-scan devices).

Figure 1:
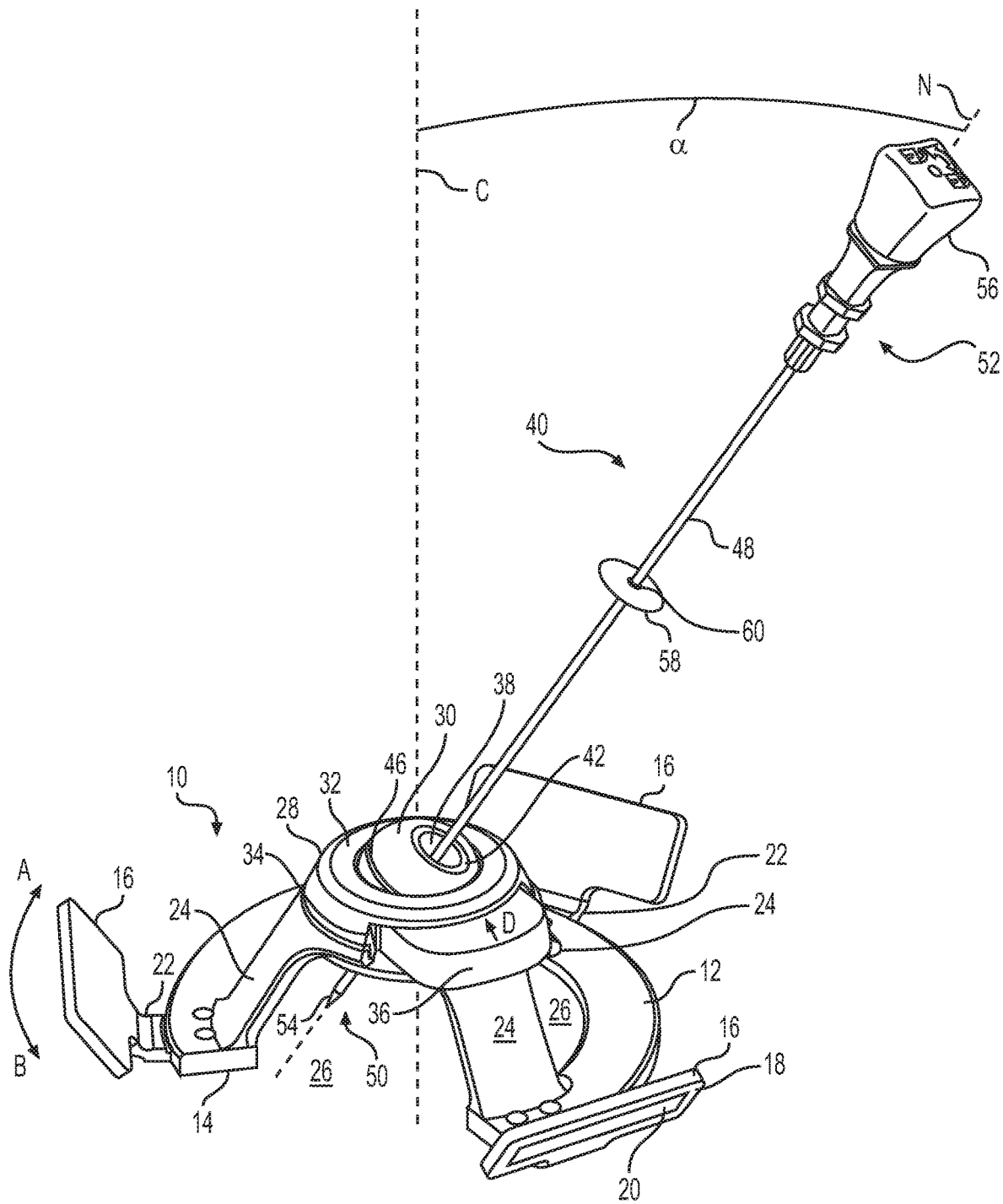
- FIG. 1 illustrates an exemplary guidance system including a base and an insertion device, according to an aspect of the present disclosure.

As shown in FIG. 1, a surgical guidance system comprises a base 10 including a base member 12. Base member 12 may be a substantially planar disc, washer, plate, and/or ring. For example, base member 12 as shown in FIG. 1 includes a C-shaped plate extending between about 220° and about 260°, or about 240° about a central axis C of base 10. In other words, base member 12 is a partial ring. Base member 12 includes a distally directed surface 14 which may be moved along the skin of a patient, as will be described in further detail below.

Base member 12 includes a plurality of tabs 16 extending radially outward (e.g., away) from central axis C. As shown, central axis C extends perpendicular to a plane of distally directed surface 14. Three tabs 16 are equidistantly spaced about base member 12. Alternatively, more or fewer tabs 16 may be positioned about base member 12, either equidistantly or non-equidistantly spaced. Tabs 16 may be any appropriate shape. For example, as shown in FIG. 1, tabs 16 are generally rectangular in shape. Other shapes may include square, circular, oval, triangular, polygonal, irregular shapes, and combinations thereof. Further, in some arrangements, at least one tab 16 may have a shape different than a shape of at least one other tab 16. As shown, each tab 16 may be generally planar and include a distally directed surface 18 which may be selectively fixed to the skin of the patient, as will be described in further detail below. Accordingly, distally directed surface 18 may include an adhesive 20 or tape positioned thereon. In another arrangements, only one or some of the tabs 16 may include adhesive 20 thereon. Alternatively, in some arrangements, none of tabs 16 include adhesive 20 thereon. Rather, once positioned at a desired location on the skin of a patient, a medical professional may tape or glue or otherwise secure one or more of tabs 16 to the skin of the patient.

Each tab 16 is coupled to base member 12 via at least one flexible living hinge 22 thereby enabling movement of tabs 16 with respect to base member 12. For example, living hinge 22 may include a connection between tabs 16 and base member 12 having a thinned dimension thereby enabling bending along the thinned portion. Accordingly, in a first configuration, as shown in FIG. 1, each tab 16 may be flexed upward or away from a plane of distally directed surface 14 in the direction of arrow A. In a second configuration, not shown, each tab 16 may be pushed or deflected downward towards a plane of distally directed surface 14 in the direction of arrow B, as will be described in further detail below. It is understood that each tab 16 is independently deflectable in the directions of arrow A or arrow B such that only one or some of tabs 16 may be deflected at any one given time.

As shown in FIG. 1, base 10 further includes a plurality of legs 24. For example, base 10 includes three equidistantly spaced legs 24 (only two visible in the orientation of FIG. 1). In other arrangements, more or fewer legs 24 may be positioned about base 10, either equidistantly or non-equidistantly spaced about central axis C. Each of legs 24 may have any appropriate shape and pairs of adjacent legs 24 may define a window 26 to facilitate insertion/removal of various tools or devices (e.g., sheaths, needles, etc.), as needed. A width (extending along a plane parallel with the plane of the distally directed surface 14) of each leg 22 has a smaller dimension than a length extending between base member 12 and a support or mount 28. As such, windows 26 may be sized to pass one or more tools therethrough, if determined to be necessary or desired by the medical professional. Accordingly, in some aspects, legs 24 may have a length of between about 5 mm and 25 mm, or about 20 mm. Additionally, since base member 12 is C-shaped, at least one window 26 is enlarged relative to at least one of the other windows 26. That is, at least one window 26 is free from (e.g., does not include) base member 12 along a bottom portion thereof. As such, base member 12 does not reduce the size of window 26 and/or does not impede or interfere with insertion/removal of tools along the skin of a patient through base 10.

Mount 28 comprises a ball socket within which an insertion device guide, such as sphere or ball 30, is moveably received. For example, mount 28 may be contoured (not shown) (e.g., concave, cup-shaped, etc.) in a manner corresponding to a shape of ball 30 so as to enable rotational movement of ball 30 within mount 28. As such, ball 30 is rotatable 360° about central axis C. Additionally, ball 30 may be angled at an angle α, extending between central axis C and a longitudinal axis N of an insertion device 40 received within ball 30. For example, angle α may be between about 10° and about 45°, or about 35°. It is understood that that ball 30 is further rotatable about axis N, which in some arrangements, may be coaxial or angled with respect to central axis C In some arrangements, a lubricious material may be positioned between or on one or both of mount 28 and ball 30 so as to reduce friction between mount 28 and ball 30. As shown, mount 28 may include a lip or rim 32 extending radially inwardly toward central axis C so as to retain ball 30 within mount 28.

Mount 28 includes a passage 34 extending through a portion (e.g., a radially outward side) thereof, as shown in FIG. 1. A lock 36 is movably received within passage 34 and may be selectively actuated so as lock ball 30 in a selected position. For example, lock 36 may include a push button mechanism. In a first configuration (e.g., a locked configuration), as shown in FIG. 1, a spring (not shown) of lock 36 frictionally engages ball 30, thereby preventing relative movement between ball 30 and mount 28. In a second configuration, not shown, lock 36 may be depressed or pushed radially inwardly in the direction of arrow D so as to release the spring force imparted by the spring of lock 36 so as to enable or permit ball 30 to move freely within mount 28. In some arrangements, lock 36 may comprise a spring-loaded button or push tab.

Ball 30 includes a through hole 38 through which an insertion device 40 may be advanced, as will be described in further detail below. Through hole 38 extends between a proximal entry opening 42 and a diametrically opposed distal exit opening 44 (not visible in the orientation of FIG. 1). As shown, entry opening 40 may be tapered, conical, or otherwise funnel-shaped so as to facilitate passage of insertion device 40 therethrough. A silicone, rubber, semi-rigid or elastomeric material may line or be included in through hole 38 so as to frictionally engage insertion device 40. Alternatively, through hole 38 may have a diameter sufficiently similar in size to a diameter of a portion of insertion device 40 extending therethrough so as to frictionally grip insertion device 40. In either arrangement, insertion device 40 is securely positioned within through hole 38, and may be advanced upon application of a force greater than the frictional force retaining insertion device 40 within through hole 38. Additionally, a radiopaque member 46 is positioned on ball 30. For example, radiopaque member 46 may include a ring or wire of radiopaque material extending circumferentially about a hemisphere of ball 30. In some arrangements, however, radiopaque member 46 may extend about less than the entire circumference of ball 30. Additionally, in some arrangements, radiopaque member 46 may be discontinuous about the circumference of ball 30. Still further, in some arrangements, radiopaque member 46 may be located on either side of the hemisphere of ball 30.

An exemplary insertion device 40 is illustrated in FIG. 1 as having an elongated body or shaft 48 extending along axis N between distal end 50 and a proximal end 52. Insertion device 40 may be any type of elongated object, such as a needle, a cannula, a catheter with one or more working channels, a rigid or flexible tube, or like element. In some arrangements, insertion device 40 is an 18 or 21 gauge insertion needle. Distal end 50 has a sharpened or angled tip 54 configured or arranged to facilitate penetration of bodily tissue (e.g., into and/or through the skin of a patient). At least a portion of distal end 50 includes a radiopaque material to enhance visualization of insertion device 40 via fluoroscopy. For example, in some arrangements, the entirety of shaft 48 may be radiopaque, while in other arrangements, one or more portions of shaft 48 may be radiopaque.

Proximal end 52 has a hub or interface 56 engageable with a manipulation tool. For example, in some arrangements, interface 56 includes a polygonal shape engageable with a forceps (not shown). In other arrangements, however, proximal end 52 may assume any suitable shape, such as circular of spherical shape, which may have a portion configured for use with forceps, such as interface 56. Additionally or alternatively, interface 56 may be gripped with the hand of the medical professional, as will be described in further detail below. In some aspects, interface 56 may be coupled with a syringe (not shown) or the like for aspiration and/or injection of fluid (e.g., urine), as will be described in further detail below. Optionally, insertion device 40 may include a depth indication slider 58, which may be movably coupled to shaft 48. For example, slider 58 includes a central through hole 60 about shaft 48. A silicone, rubber, semi-rigid or elastomeric material may line or be included in through hole 60 so as to frictionally engage shaft 48. Alternatively, through hole 60 may have a diameter sufficiently similar in size to a diameter of a portion of insertion device 40 extending therethrough so as to frictionally grip insertion device 40. In either arrangement, insertion device 40 is securely positioned within through hole 60. In use, slider 58 may be advanced to a location along shaft 48 indicative of a maximum or preferred depth of insertion of distal end 50 into tissue of the patient. The position of slider 58 may be adjusted by the user via application of a force greater than the frictional force retaining insertion device 40 within through hole 60 and then advancing or retracting slider 58 along shaft 48. In some arrangements, however, slider 58 may be omitted.

Figure 2:
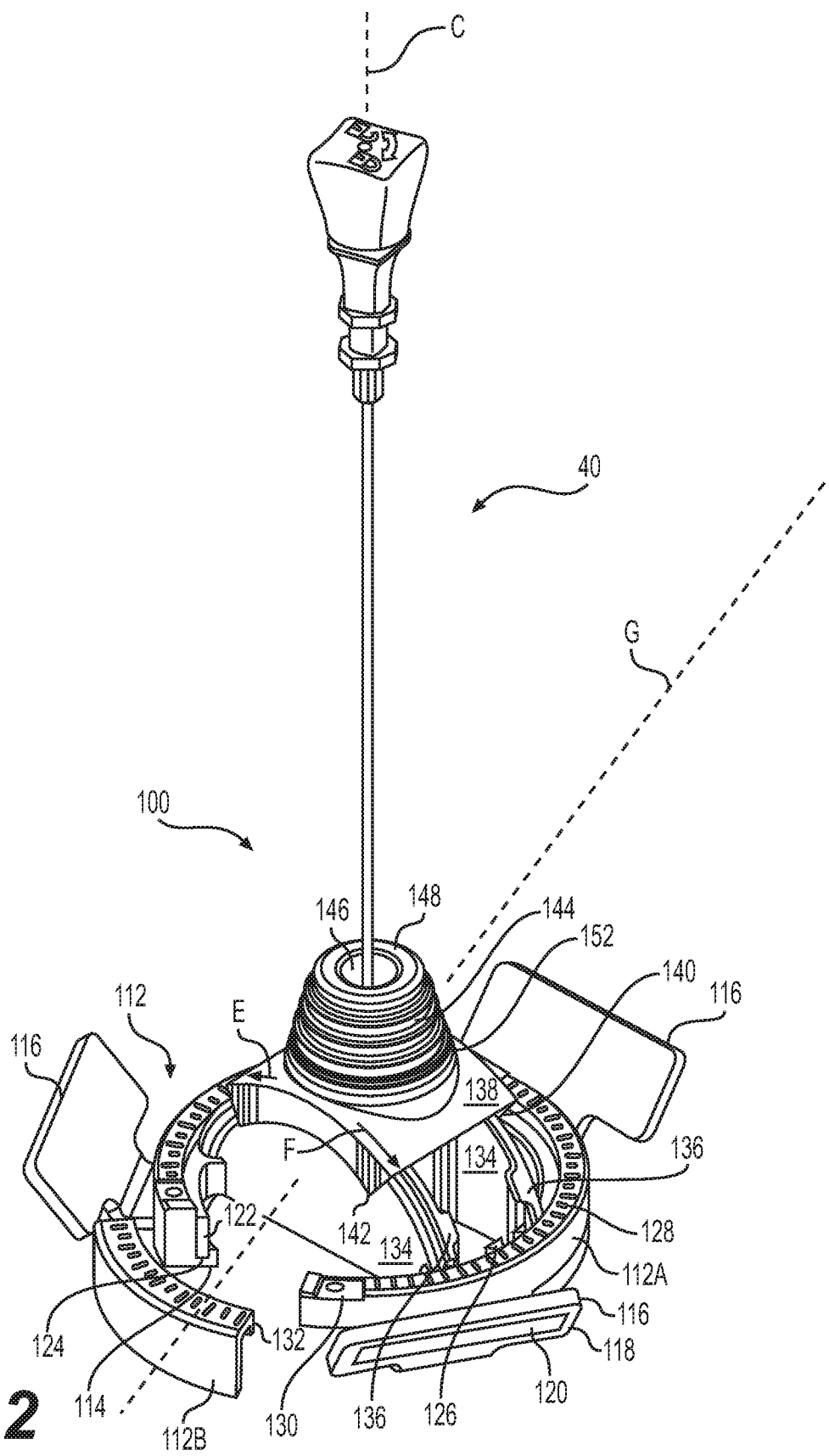
FIG. 2 illustrates an exemplary guidance system including a base and an insertion device, according to a further aspect of the present disclosure.

A surgical guidance system according to a further aspect is illustrated in FIG. 2. The system of FIG. 2 is similar to the system of FIG. 1, but with base 10 having been replaced with base 100. As shown, base 100 includes a partial ring 112A and an insert 112B, collectively forming a base member 112. Upon connection of insert 112B to partial ring 112A, base 100 includes a full 360° ring having a distally directed surface 114 which may be moved along the skin of a patient, as will be described in further detail below. In some arrangements, for example, partial ring 112A extends between about 245° and about 305°, or about 275° about a central axis C (along which insertion device 40 extends in the orientation of FIG. 2) of base member 112. Additionally, in some arrangements, insert 112B extends between about 55° and about 115°, or about 85° about central axis C of base member 112. Insert 112B may be selectively coupled and uncoupled to partial ring 112A in any appropriate manner. In some arrangements, one or more portions of partial ring 112A may be magnetically attracted to one or more portions of insert 112B. Additionally or alternatively, partial ring 112A may include one or more insert connection portions 130 defining a recess for connection (e.g., a snap-fit connection, or the like) to a corresponding lip or extension 132 of insert 112B.

Similar to base member 12 of FIG. 1, base member 112 of FIG. 2 includes a plurality of tabs 116 extending radially outward (e.g., away) from central axis C of base member 112. As shown, central axis C extends perpendicular to the plane of distally directed surface 114. Similar to base 12, tabs 116 may have any appropriate shape, quantity, arrangement, and/or spacing. Additionally, each tab 116 may be generally planar and include a distally directed surface 118 which may be selectively fixed to the skin of the patient, as will be described in further detail below (e.g., via optional adhesive 120 or tape).

Base 100 further includes a support 122. As shown, at least a portion of support 122 is received within a channel or track 124 of partial ring 112A. Similar to partial ring 112A, support 122 may be C-shaped and extend between about 245° and about 305°, or about 275° about central axis C. Support 122 is rotatable about central axis C to adjust an angular position of insertion device 40. As shown, support 122 includes an indicator 126. During rotation of support 122, indicator 126 is aligned with one of a plurality of angular graduations 128 disposed about base member 112. As such, an angular rotation of support 122, and thereby insertion device 40 extending therethrough, is readily visible to the medical professional. Additionally, at least one of support 122 and base member 112 may include a ratcheted, a notched, an indented, or similar shaped surface (not shown) such that rotation of support 122 about base member 112 results in tactile feedback and/or audible feedback (e.g., a clicking noise) due to interference between support 122 and base member 112.

As shown in FIG. 2, support 122 further includes a pair of arms 134. Arms 134 are fixed relative to support 122 so as to rotate therewith. As shown, each arm 134 includes a hemispherical shape having a rail 136. Each rail 136 may be coupled to a mount or a support bed 138. That is, support bed 138 may include a track or rim 140 coupled to rails 136 for movement there along. A silicone, rubber, semi-rigid and/or elastomeric material may line or be included between rim 140 and rails 136 to frictionally retain support bed 138 at a desired location along rails 136. Alternatively, rim 140 may be sized to have a dimension sufficiently similar to a dimension of rails 136 so as to frictionally retain support bed 136 at a desired location along rails 136. Upon application of a force greater than the frictional force retaining support bed 136 at a location along rails 136, support bed 138 may be advanced or retracted along rails 136 in the direction of arrows E and F. In such a manner, an angular position of support bed 138 relative to an axis G perpendicular to central axis C may be adjusted. As shown, support bed 138 includes a plurality of indicia 142 indicative of an angle of adjustment of support bed 138 relative to the axis G, and may align with indicia (not shown) on arms 134.

Support bed 138 further includes an insertion device guide mount 144 having a through hole 146 through which insertion device 40 may be advanced, as will be described in further detail below. Through hole 146 extends between a proximal entry opening 148 and a diametrically opposed distal exit opening (not visible in the orientation of FIG. 2). Similar to ball 30 of FIG. 1, entry opening 148 may be tapered, conical, or otherwise funnel-shaped so as to facilitate passage of insertion device 40 therethrough. Additionally, a silicone, rubber, semi-rigid, and/or elastomeric material may line or be included in through hole 146 so as to frictionally engage insertion device 40. Alternatively, through hole 146 may have a diameter sufficiently similar in size to a diameter of a portion of insertion device 40 extending therethrough so as to frictionally grip insertion device 40. In either arrangement, insertion device 40 is securely positioned within through hole 146, and may be advanced upon application of a force greater than the frictional force retaining insertion device 40 within through hole 146. Additionally, a radiopaque member 152 may be positioned on mount 144. For example, radiopaque member 152 may include a ring or wire of radiopaque material extending circumferentially about at least a portion or all of mount 144. In this arrangement, insertion device 40 may be rotated about base member 112 and along arms 134, all the while being located at the center of base member 112 thereby facilitating accurate insertion along a desired angle.

Additionally, in some arrangements, radiopaque member 152 may be discontinuous about the circumference of mount 144.

Figure 3:
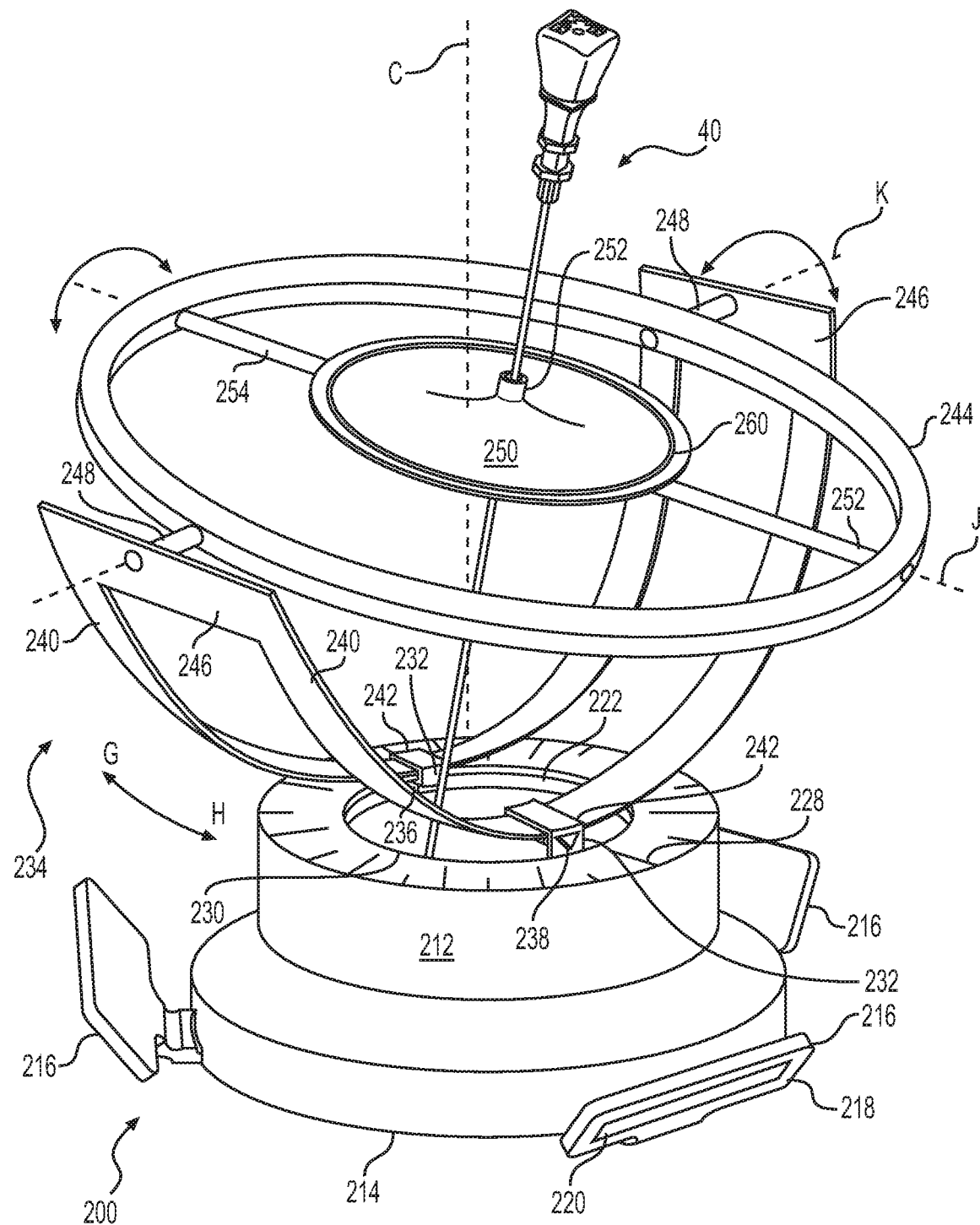
FIG. 3 illustrates an additional exemplary guidance system including a base and an insertion device, according to a further aspect of the present disclosure.

A surgical guidance system according to a further aspect is illustrated in FIG. 3. The system of FIG. 3 is similar to the system of FIG. 1, but with base 10 having been replaced with base 200. Base 200 includes a base member 212 having a distally directed surface 214 which may be moved along the skin of a patient, as will be described in further detail below. Base member 212 may have any appropriate shape (e.g. circular, ovular, polygonal, irregular, combinations thereof, or the like). Additionally, base member 212 may have a shape or size that varies along the length of base member 212. Base member 212 includes a central through hole 230 extending therethrough. Similar to base member 12 of FIG. 1, base member 212 of FIG. 3 includes a plurality of tabs 216 extending radially outward (e.g., away) from central axis C of base member 212. As shown, central axis C extends perpendicular to the plane of distally directed surface 214. Similar to base 12, tabs 216 may have any appropriate shape, quantity, arrangement, and/or spacing. Additionally, each tab 216 may be generally planar and include a distally directed surface 218 which may be selectively fixed to the skin of the patient, as will be described in further detail below (e.g., via optional adhesive 220 or tape).

Base member 212 further includes a channel 222 extending about an internal circumference of base member 212, within through hole 230. Alternatively, channel 222 may extend about an external circumference of base member 212, without departing from the scope of this disclosure. In either arrangement, channel 222 may be sized to receive at least one projection 232 of a mount 234. For example, mount 234 may include a pair of diametrically opposed projections 232, at least a portion 236 of which is received within and rotatable about channel 222. Accordingly, mount 234 is rotatable about central axis C of base 200 to adjust an angular position of insertion device 40. As shown, mount 234 may include an indicator 238 on at least one of projections 232. During rotation of mount 234, indicator 238 is aligned with one of a plurality of angular graduations 228 disposed about base member 212. As such, an angular rotation of mount 234 about central axis C, and thereby insertion device 40 extending therethrough, is readily visible to the medical professional. Additionally, at least one of portion 236 and channel 222 may include a ratcheted, a notched, an indented, or similar shaped surface (not shown) such that rotation of mount 234 about base member 212 results in tactile feedback and/or audible feedback (e.g., a clicking noise) due to interference therebetween.

As shown in FIG. 3, mount 234 includes a hemispherical frame having a pair of opposed legs 240. Each leg 240 is received with a coupling 242 of a respective one of projections 232. For example, coupling 242 includes at least one bracket, ring, pipe, and/or tube within which a leg 240 is movably received. That is, legs 240 are movable (e.g., slidable) relative to couplings 242 to adjust an angle of insertion device 40. For example, legs 240 of mount 234 may be selectively moved in the direction of arrow G (e.g., out of the page as shown in FIG. 3) or in the direction of arrow H (e.g., into the page as shown in FIG. 3) about an axis J extending perpendicular to central axis C. A silicone, rubber, or a semi-rigid or elastomeric material may line or be included in couplings 242 so as to frictionally engage legs 240. Alternatively, couplings 242 may have a size sufficiently similar to leg 240 extending therethrough so as to frictionally grip leg 240. In either arrangement, mount 234 is securely positioned within couplings 242, and may be advanced/retracted upon application of a force greater than the frictional between legs 240 and couplings 242.

Base 200 further includes a ring 244 pivotably coupled to mount 234. For example, mount 234 includes a pair of struts 246 extending between legs 240. For example, a first strut 246 extends between first ends of legs 240 while a second strut 246 extends between second ends of legs 240 so as to form the hemispherical frame of mount 234. Each strut 246 is pivotably coupled to ring 244 via a shaft 248 extending therebetween. As such, ring 244 is rotatable about an axis K which is perpendicular to central axis C and axis J.

Base 200 further includes an insertion device guide such as a central support 250 within ring 244. Central support 250 includes a through hole 252 through which an insertion device 40 may be advanced, as will be described in further detail below. A silicone, rubber, or a semi-rigid or elastomeric material may line or be included in through hole 252 so as to frictionally engage insertion device 40. Alternatively, through hole 252 may have a diameter sufficiently similar in size to a diameter of a portion of insertion device 40 extending therethrough so as to frictionally grip insertion device 40. In either arrangement, insertion device 40 is securely positioned within through hole 252, and may be advanced upon application of a force greater than the frictional force retaining insertion device 40 within through hole 252. Central support 250 is pivotably coupled to ring 244 via a shaft 254 extending therebetween. In such a manner, central support 250, and insertion device 40 extending therethrough, is pivotable about axis J extending perpendicular to central axis C and axis K. A radiopaque member 260 may be positioned on central support 250. For example, radiopaque member 260 may include a ring or wire of radiopaque material extending circumferentially about at least a portion or all of central support 250. Additionally, in some arrangements, radiopaque member 260 may be discontinuous about the circumference of central support 250.

Figure 4:
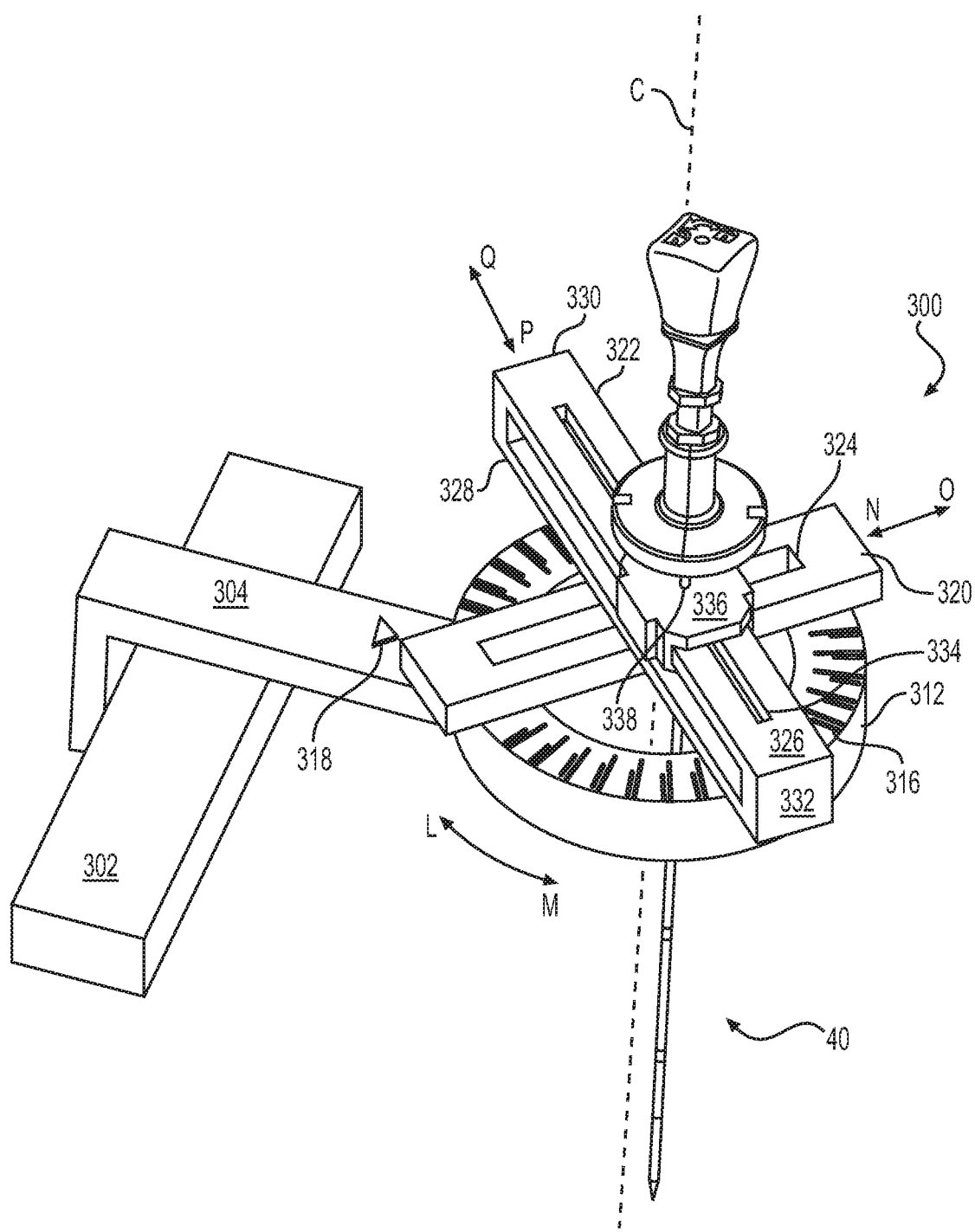
FIG. 4 illustrates another exemplary guidance system including a base and an insertion device, according to a further aspect of the present disclosure.

A surgical guidance system according to a further aspect is illustrated in FIG. 4. The system of FIG. 4 includes a base 300 coupled to a bed 302 via an arm 304. For example, bed 302 may include an operating table and/or a hospital bed on which a patient may be positioned for surgery, and is schematically illustrated in FIG. 4. Arm 304 may extend between bed 302 and base 300 and may include any one or more of struts, supports, brackets, and/or linkages to facilitate support and mounting of base 300 to bed 302. In some arrangements, a rack and pinon mechanism may couple bed 302 to arm 304.

Base 300 includes a base member 312 having a central through hole 314 extending therethrough. Base member 312 is rotatably coupled to arm 304 such that base member 312 is rotatable about central axis C of base 300 e.g., in the direction of arrow L and/or arrow M. For example, arm 304 may include a post (not shown) which is received within a track or channel (not shown) on a surface of base member 312 facing arm 304 (e.g., an underside or bottom of base member 312). The channel may include cutouts, notches, or the like such that movement of the post of 304 along the channel of base member 312 provides a tactile and/or audible feedback. As shown, base member 312 includes angular graduations 316 disposed about base member 312 while arm 304 includes an indicator 318. During rotation of base member 312, indicator 318 is aligned with one of the plurality of angular graduations 316 disposed about base member 312. As such, an angular rotation of support base member 312, and thereby insertion device 40 extending therethrough, is readily visible to the medical professional.

Base 300 further includes a first linear adjuster 320 and a second linear adjuster 322 extending perpendicularly to first linear adjuster 320. First linear adjuster 320 is fixedly mounted (e.g., non-movably mounted) to base member 312 while second linear adjustor 322 may move (e.g., slide, translate, etc.) in a first direction N or a second direction O opposite first direction N, along first linear adjuster 320. For example, first linear adjustor 320 includes a central through hole 324 within which a projection (not shown) of second linear actuator 322 extends. The projection may include an enlarged portion (not shown) having a dimension larger than a dimension (e.g., width) of through hole 324 so to maintain second linear actuator 322 coupled (e.g., movably coupled, slidably coupled, etc.) to first linear actuator 320. Second linear adjuster 322 is rectangular and includes a first side surface 326, a second side surface 328, a first base surface 330, and a second base surface 332. First and second base surfaces 330 and 332 extend between opposite ends of first and second side surfaces 326 and 328. Additionally, second linear adjuster 322 includes a central through hole 334 extending through first and second side surfaces 326 and 328. An insertion device guide mount 336 is moveably (e.g., slidably) coupled to first side surface 326. Mount 336 is moveable in a first direction P and a second direction Q opposite first direction P, along second linear adjuster 322. Additionally, mount 336 includes a central through hole 338 though which insertion device 40 extends. A silicone, rubber, semi-rigid, and/or elastomeric material may line or be included in through hole 338 so as to frictionally engage insertion device 40. Alternatively, through hole 338 may have a diameter sufficiently similar in size to a diameter of a portion of insertion device 40 extending therethrough so as to frictionally grip insertion device 40. In either arrangement, insertion device 40 is securely positioned within through hole 338, and may be advanced upon application of a force greater than the frictional force retaining insertion device 40 within through hole 338. In use, insertion device 40 is advanced to second linear adjuster 322 until accurate placement is determined, and then further advanced through second linear adjuster 322 and first linear actuator 320 to insert insertion device 40.

In use, a medical professional may use any of base 10, base 100, base 200, or base 300 to align insertion device 40 with a desired treatment location, e.g., a target calyx of a kidney. Optionally, prior to or during a procedure (e.g., a PCNL procedure), the patient may be directed to ingest a radiopaque contrast dye. Alternatively, one or more portions or structures of the patient, e.g., a target calyx in a kidney, may be injected with radiopaque contrast dye. In such a manner, the target calyx or other structure can be visualized via fluoroscopy.

Next, the medical professional may move base 10, base 100, base 200, and/or base 300 relative to the skin of the patient. For example, the medical professional may translate, slide, or otherwise move distally directed surface 14, 114, 214 of base member 12, 112, 212, respectively, along the skin of a patient. Alternatively, the medical professional may move base 312 via arm 318 over (e.g., above the body of the patient). In order to determine the proper angle of insertion of insertion device into the target calyx, a medical professional, with the aid of a fluoroscopy device, may adjust insertion device 40 relative to base 10, base 100, base 200, and/or base 300. For example, the medical professional may rotate ball 30 within mount 28 of base 10 about central axis C and/or position ball 30 at angle α with respect to central axis C (FIG. 1); may rotate support 122 relative to base member 112 and/or adjust a location of support bed 138 along rails 136 about axis G (FIG. 2); may adjust mount 234 relative to base 212 about central axis C, adjust legs 240 relative to couplings 242 about axis J, adjust ring 244 about axis K, and adjust central support 250 about axis J (FIG. 3); or adjust base member 312 about central axis C, adjust second linear adjuster 322 along first linear adjustor 320 in direction N and/or O, and/or adjust mount 336 along second linear adjustor 322 in direction Q and/or P (FIG. 4).

During adjustment of insertion device 40 relative to base 10, base 100, base 200, and/or base 300, the medical professional may view one or more radiopaque portions of base 10, base 100, base 200, base 300, insertion device 40, and the target calyx. For example, the medical professional may observe the location of radiopaque ring 46, 152, and/or 260 relative to the insertion device 40 and target calyx. Once the radiopaque ring 46, 152, and/or 260 is in line with axis N of insertion device 40 and the target calyx, the proper insertion angle is identified. At this point, tabs 16, 116, and/or 216 may be deflected towards the plane of distally directed surface 14, 114, and/or 214 so as to contact and stick the skin of the patient via adhesive 20, 120, and/or 220. Alternatively, tabs 16, 116, and/or 216 may be secured to the skin of the patient via one or more of glue or tape.

Upon confirming an appropriate angle of insertion of insertion device 40, the medical professional may rotate a C-arm of the fluoroscopy device to an angle perpendicular to the angle at which it was positioned when the angle of insertion of insertion device 40 was identified. In such an orientation, the fluoroscopy device enables a clear view of the depth of insertion of insertion device 40. Following confirmation of the angle of insertion and rotation of the C-arm of the fluoroscopy device, insertion device 40 may be advanced (e.g., moved distally along axis N) through through hole 38, 148, 252, and/or 338 to penetrate the skin of the patient and advance tip 54 to a target location within the body of the patient (e.g., a target calyx). For example, a medical professional may grasp interface 56 (or any other available portion of insertion device 40) via a tool (e.g., forceps) or their hand so as to advance insertion device 40 distally towards the target calyx. A proper depth of insertion of insertion device 40 may be confirmed in any appropriate manner, e.g., via visualization of one or more radiopaque portions of insertion device 40, visual confirmation of urine coming through the needle, aspiration of urine through a syringe connected to the needle, or some combination of the above. A guidewire may be inserted through the shaft 48 and the shaft 48 may be removed over the guidewire. The guidewire may be left to guide instruments necessary to the PCNL procedure into the target calyx, such as dilating catheters, access sheaths, lithotripsy devices, retrieval devices and the like.

Figure 5A:
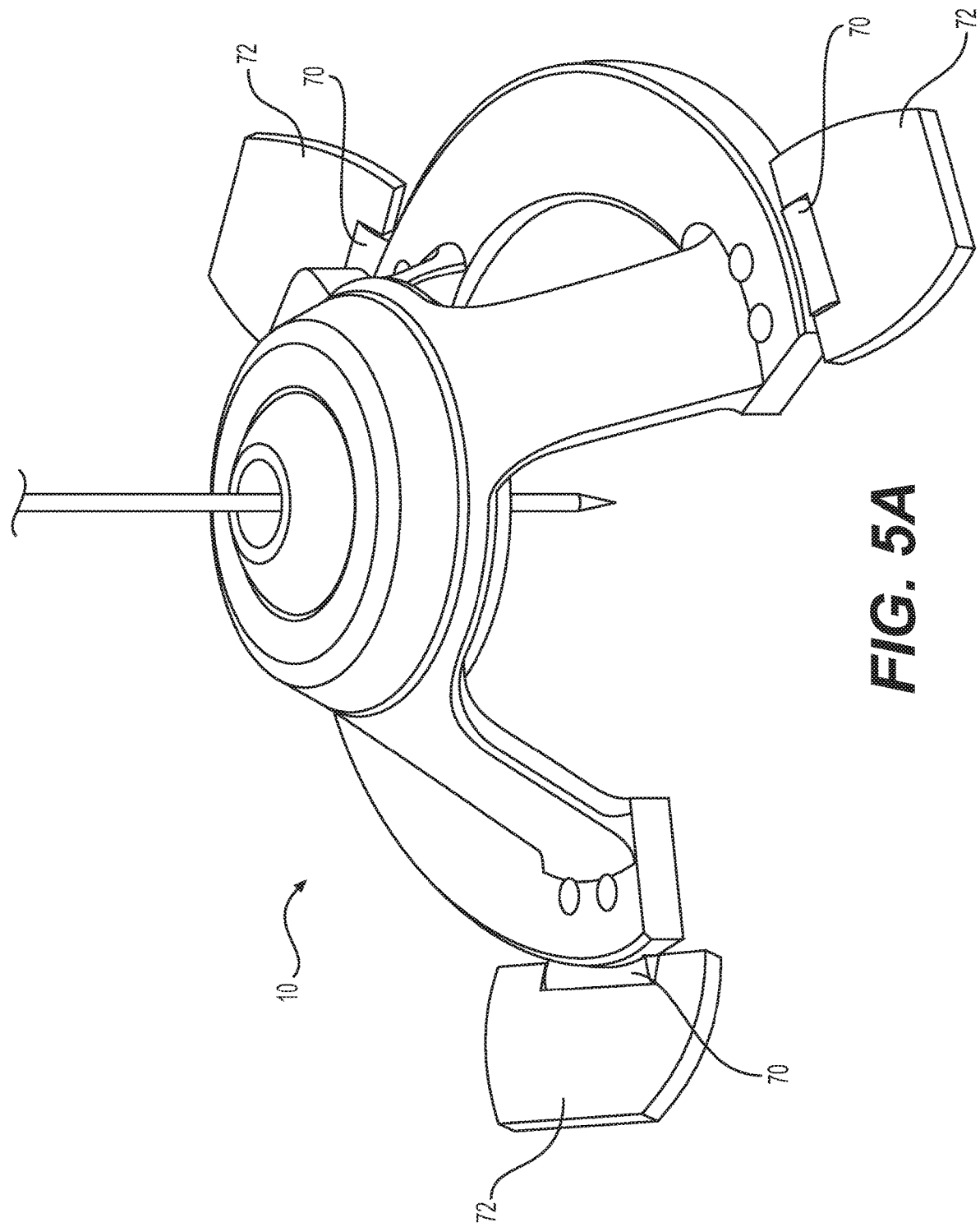
FIGS. 5A-5C illustrate various alternative attachment mechanisms of the bases of FIGS. 1-3.
Figure 5B:
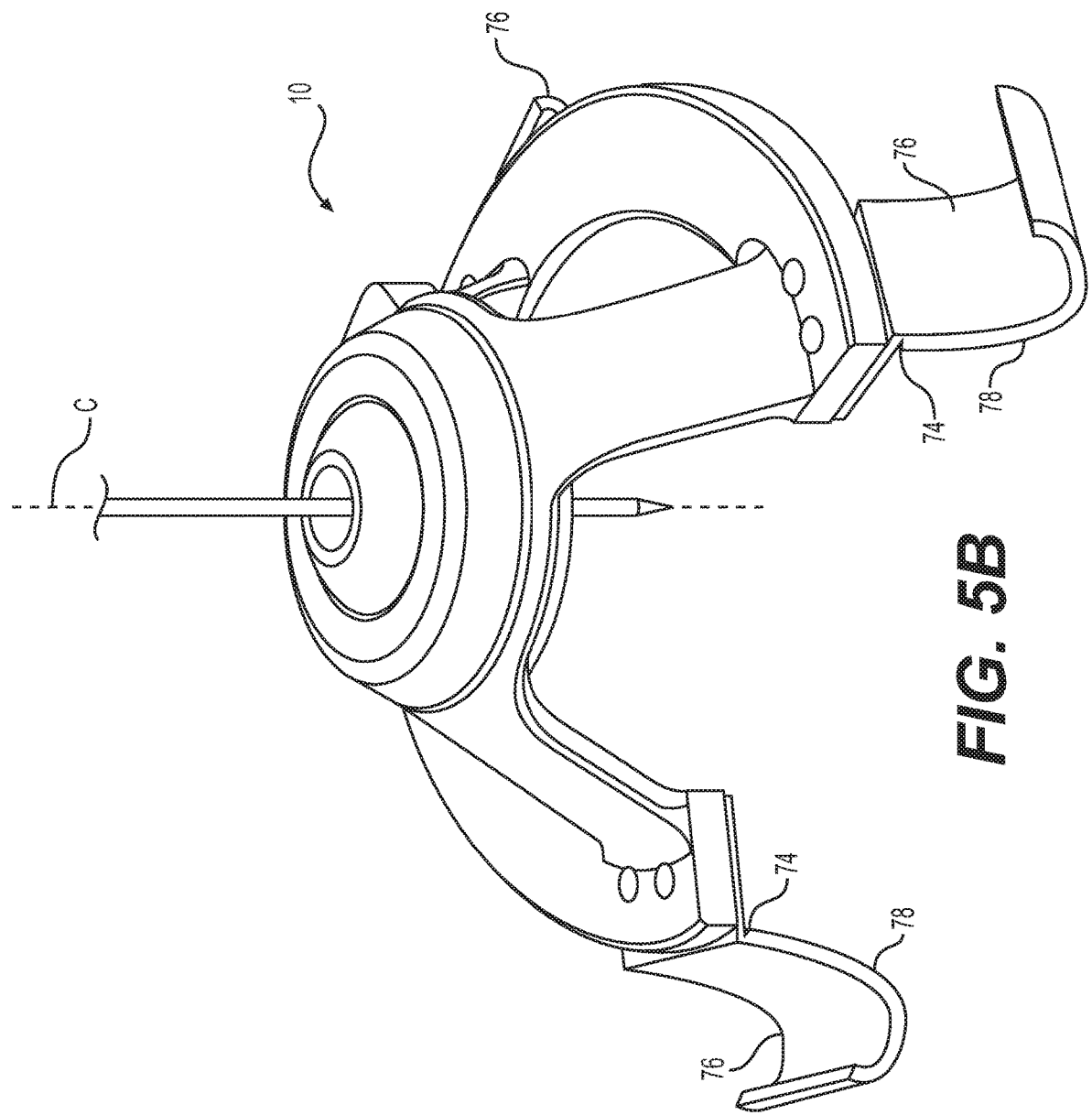
Figure 5C:
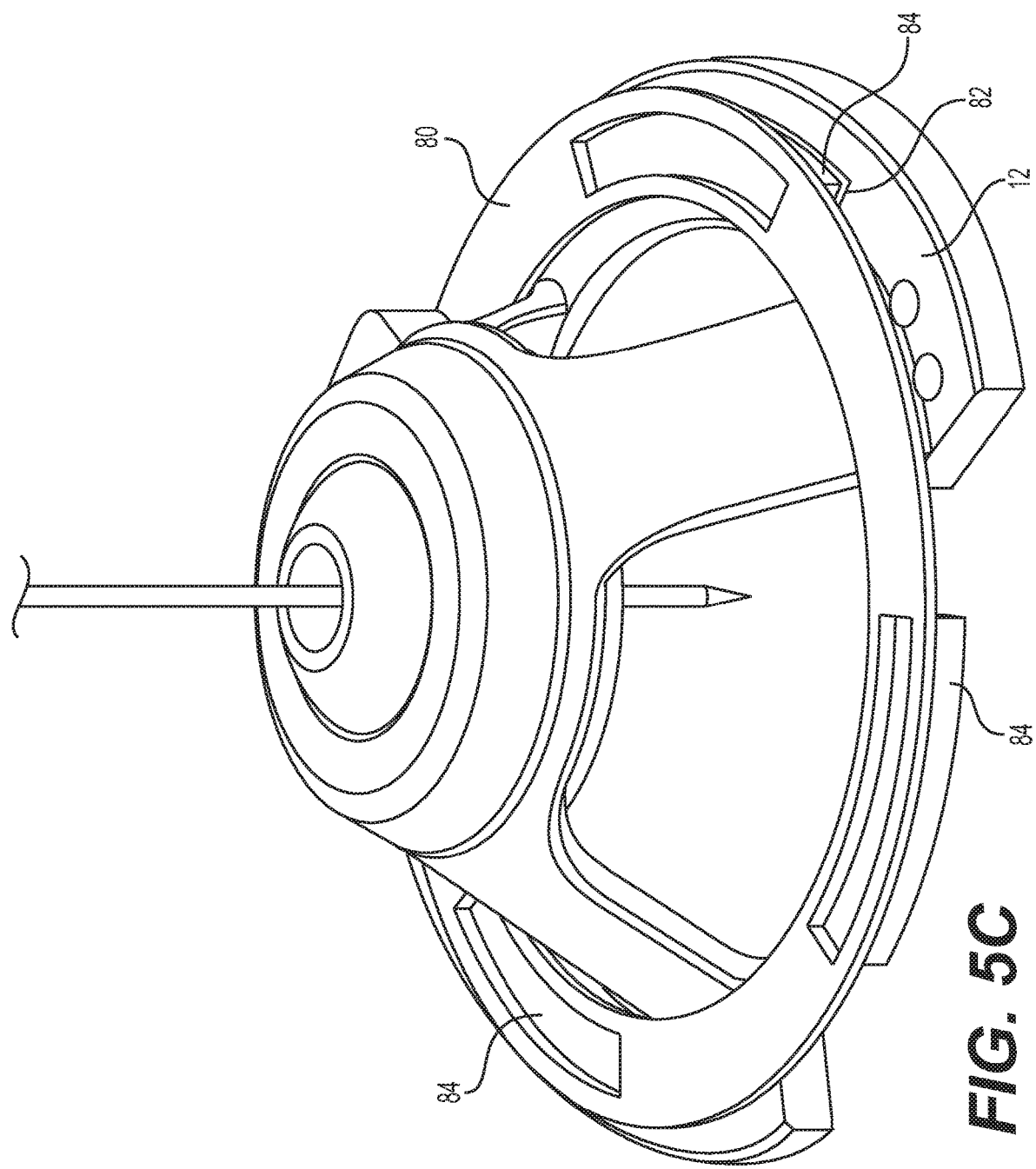

FIGS. 5A-5C illustrate alternative tab constructions of the bases of FIGS. 1-3. For example, as shown in FIG. 5A, living hinges 22 of base 10 of FIG. 1 have been replaced pivot members 70 about which tabs 72 may be pivoted. To secure tabs 72 of FIG. 5A the skin of the patient, tabs 72 are pivoted via a respective pivot member 70 toward the skin of the patient. Similar to the arrangement of FIG. 1, a distal facing surface of one or more tabs 72 include an adhesive (not shown) thereon. Alternatively, as shown in FIG. 5B, living hinges 22 and tabs 16 of base 10 of FIG. 1 have been replaced with living hinges 74 and legs 76. As shown, the legs 76 may elevate base member 12 from the skin of the patient by a distance equal to the length of legs 76. To secure legs 76 to the skin of the patient, base member 12 may be depressed distally, e.g., toward the skin of the patient to flex legs 76 radially away from central axis C along living hinges 74. Alternatively, any one or more of legs 76 may be pushed or pulled radially outwardly away from central axis C so as to flex legs 76 along living hinge 74. In some arrangements, one or more surfaces, such as inner surface 78 of one or more of legs 76 may include an adhesive (not shown) thereon. In a still further arrangement, as shown in FIG. 5C, tabs 16 of base 10 of FIG. 1 have been replaced with a ring 80. In such an arrangement, base member 12 may include one or more openings, windows, or holes 82 extending therethrough. Each hole 82 may be sized to pass an extension 84 of ring 80 therethrough. For example, each hole 82 may have a shape corresponding in size and arrangement to at least one extension 84 of ring 80. Additionally, a distally directed surface of each extension 84 may include an adhesive (not shown) thereon. To secure base 10 to the skin of the patient, ring 80 may be depressed distally, e.g., toward the skin of the patient to advance extensions 84 through holes 82.

Figure 6A:
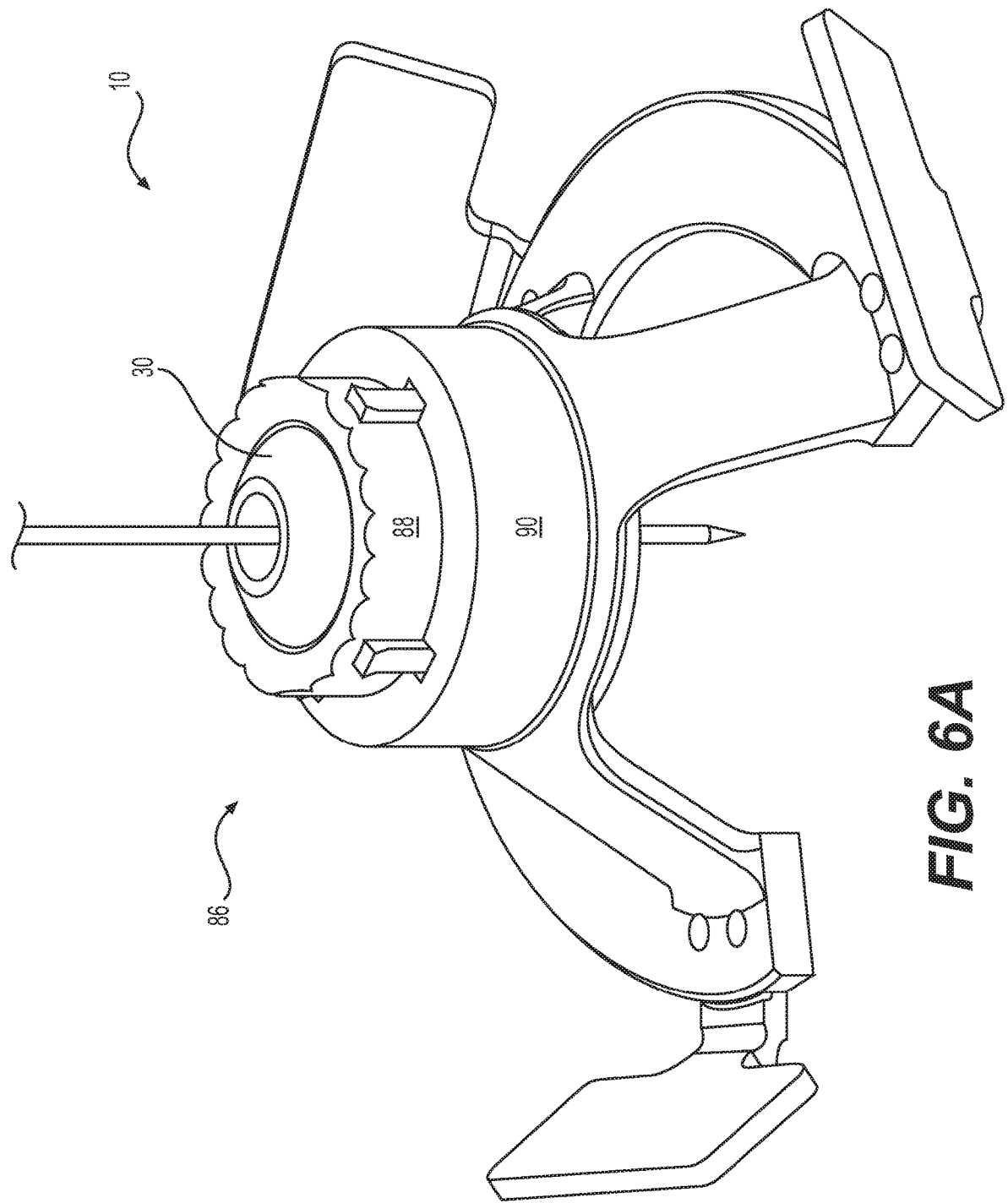
FIGS. 6A and 6B depict various alternative lock mechanisms of the base of FIG. 1.
Figure 6B:
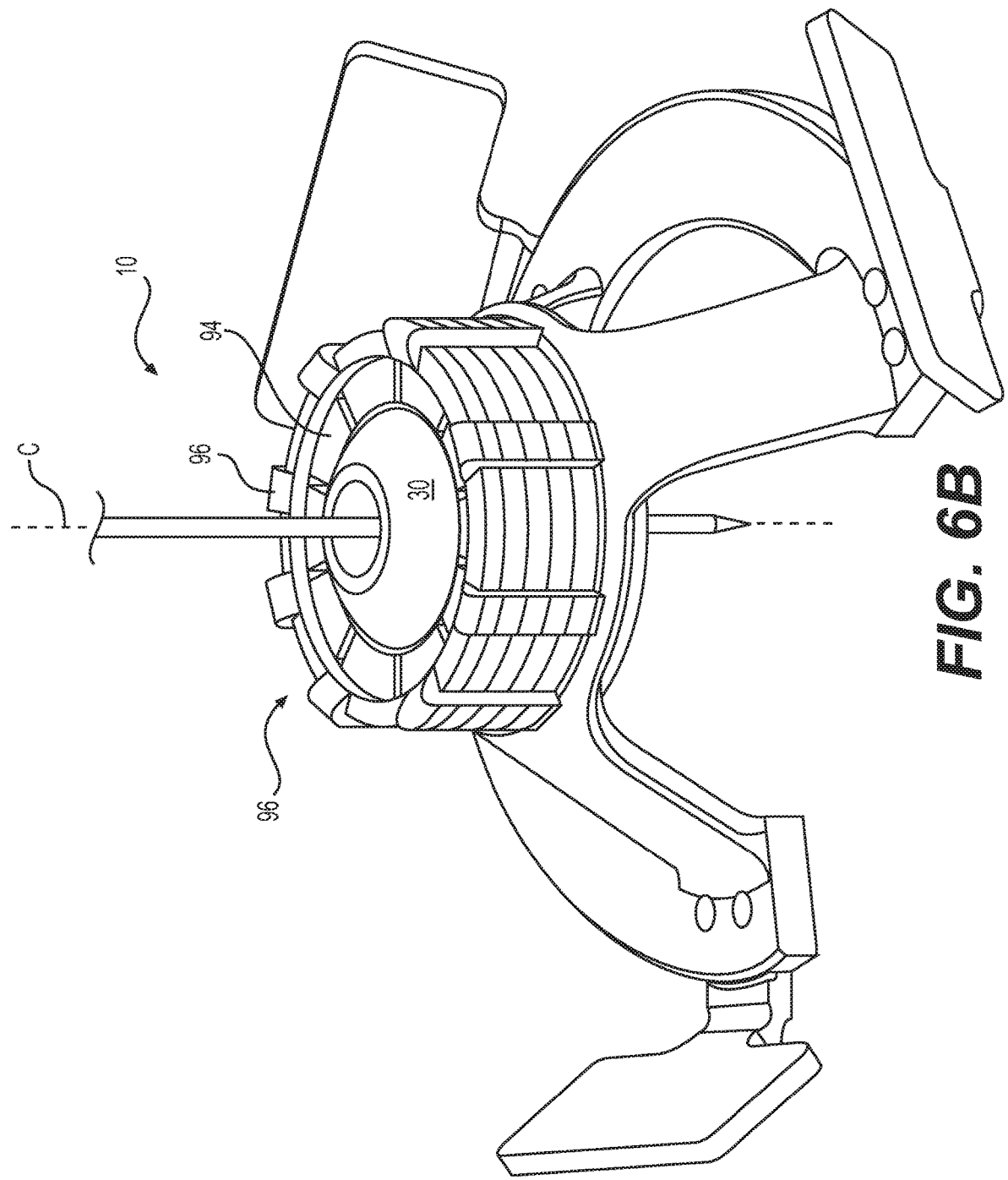

FIGS. 6A and 6B illustrate alternative lock mechanisms to secure the position of ball 30 of base 10 of FIG. 1. For example, as shown in FIG. 6A, lock 36 of base 10 of FIG. 1 has been replaced with lock 86. Lock 86 includes a spring-loaded push button 88 received within an outer housing 90. To unlock the position (e.g., the angular orientation) of ball 30 relative to a remainder of base 10, push button 88 may be depressed toward the skin of the patient so as to be received within outer housing 90. Once received therein, ball 30 may rotate relative to outer housing 90. An external surface of push button 88 may be tapered such that interference between push button 88 and outer housing 90 maintains push button 88 therein until push button 88 is once again depressed (e.g., toward an over extended configuration, not shown) so as to allow push button 88 to retract and move toward the locked configuration, as shown in FIG. 6A. In a further arrangement, as shown in FIG. 6B, lock 36 of base 10 of FIG. 1 has been replaced with lock 96. Lock 96 includes a collet 94 positioned within a collar 96. As is known, an external surface of collet 94 and an internal surface of collar 96 may be correspondingly threaded for engagement therebetween. To lock the position (e.g., the angular orientation) of ball 30 relative to a remainder of base 10, collar 96 may be rotated about central axis C so as to compress collet 94 and thereby frictionally engage ball 30.

While principles of the present disclosure are described herein with reference to illustrative aspects for particular applications, it should be understood that the disclosure is not limited thereto. For example, while slider 58 was illustrated and described in connection with the arrangement of FIG. 1, slider 58 may additionally be used in conjunction with any of the arrangements of FIGS. 2-4, 5A-5C, 6A, and 6B without departing from the scope of this disclosure. Those having ordinary skill in the art and access to the teachings provided herein will recognize additional modifications, applications, aspects, and substitution of equivalents all fall within the scope of the aspects described herein. Accordingly, the present disclosure is not to be considered as limited by the foregoing description.

We claim:

1. A guidance device, comprising:
   a base member;
   a support coupled to the base member via at least three legs, thereby defining at least a first passage, a second passage, and a third passage, each of which is configured to receive an accessory device between the base member and the support, wherein the third passage is enlarged relative to the first and second passages;
   a guide coupled to the support, wherein the guide is movable relative to the base member and includes a through hole extending therethrough; and
   a plurality of tabs coupled to the base member, wherein at least some of the plurality of tabs are deflectable toward a plane of the base member via a living hinge.

2. The guidance device of claim 1, wherein the support includes a ball socket and the guide includes a ball.

3. The guidance device of claim 2, wherein the ball is movably received within the support.

4. The guidance device of claim 2, wherein the guide includes a radiopaque member extending about a circumference of the ball.

5. The guidance device of claim 1, wherein at least some of the plurality of tabs include an adhesive thereon.

6. A guidance device, comprising:
   a base member having a central axis;
   a mount coupled to the base member;
   a ball rotatably received within the mount, wherein the ball includes a radiopaque member about a circumference of the ball;
   a lock; and
   a plurality of tabs coupled to the base member, wherein at least some of the plurality of tabs are deflectable toward a plane of the base member via a living hinge,
   wherein the ball is rotatable about a ball axis which is coaxial with or angled with respect to central axis,
   wherein the mount receives the lock, and wherein the lock includes a tab configured to be pushed radially inwards to engage or disengage with the ball.

7. The guidance device of claim 6, wherein in a locked configuration, the lock frictionally engages the ball.

8. The guidance device of claim 6, wherein at least some of the plurality of tabs include an adhesive thereon.

9. A guidance device, comprising:
   a base member;
   a support coupled to the base member via at least one leg, thereby defining at least one passage configured to receive an accessory device between the base member and the support;
   a guide coupled to the support, wherein the guide is movable relative to the base member and includes a through hole extending therethrough; and
   a plurality of tabs coupled to the base member, wherein at least some of the plurality of tabs are deflectable toward a plane of the base member via a living hinge,
   wherein the support receives a lock, the lock comprising a tab configured to be pushed radially inwards to engage or disengage with the guide.

10. The guidance device of claim 9, wherein the lock is configured to move radially outwards, after being pushed radially inwards, to disengage from the guide.

11. The guidance device of claim 9, wherein the at least one leg includes a plurality of legs.

12. The guidance device of claim 9, wherein the base member is C-shaped.

* * * * *